United States Patent
Tanaka et al.

(10) Patent No.: US 6,706,260 B1
(45) Date of Patent: Mar. 16, 2004

(54) WOUND-COVERING PREPARATION, WOUND-COVERING MATERIAL, AND METHOD OF WOUND HEALING

(75) Inventors: Shinji Tanaka, Tsukuba (JP); Ken Suzuki, Tsukuba (JP); Kenshiro Shuto, Tsukuba (JP); Akio Hayashi, Tokyo (JP); Nobuo Nakabayashi, 5-6-20, Koganehara, Matsudo-shi, Chiba 270-0021 (JP); Kazuhiko Ishihara, 3-16-37, Josuihoncho, Kodaira-shi, Tokyo 187-0022 (JP)

(73) Assignees: NOF Corporation, Tokyo (JP); Nobuo Nakabayashi, Chiba (JP); Kazuhiko Ishihara, Tokyo (JP)

( * ) Notice: Subject to any disclaimer, the term of this patent is extended or adjusted under 35 U.S.C. 154(b) by 0 days.

(21) Appl. No.: 09/743,357

(22) PCT Filed: Jul. 6, 1999

(86) PCT No.: PCT/JP99/03633

§ 371 (c)(1),
(2), (4) Date: Jan. 5, 2001

(87) PCT Pub. No.: WO00/01424

PCT Pub. Date: Jan. 13, 2000

(30) Foreign Application Priority Data

Jul. 7, 1998 (JP) .......................................... 10-192080

(51) Int. Cl.[7] .............................................. A61K 31/74
(52) U.S. Cl. .............................. 424/78.06; 424/78.02; 424/78.08; 424/78.97; 424/443; 424/445; 424/446; 424/447; 424/489; 424/501
(58) Field of Search ................................ 424/489, 501, 424/443, 445, 447, 78.08, 78.02, 78.06, 78.17

(56) References Cited

U.S. PATENT DOCUMENTS

5,711,959 A * 1/1998 Kohler et al. ................ 424/423

(List continued on next page.)

FOREIGN PATENT DOCUMENTS

EP 0 823 458 A1 2/1998

(List continued on next page.)

OTHER PUBLICATIONS

Patent Abstract of Japan, vol. 1998, No. 06, Apr. 1998, JP 10 045626, Abstract.

(List continued on next page.)

*Primary Examiner*—Thurman K. Page
*Assistant Examiner*—Liliana Di Nola-Baron
(74) *Attorney, Agent, or Firm*—Darby & Darby

(57) ABSTRACT

A wound-covering agent containing a polymer having a group represented by formula (I) (wherein $R^1$, $R^2$ and $R^3$ are the same or different and each represents hydrogen atom or $C_{1-4}$ alkyl, and m is an integer of 2 to 4); a wound-covering material containing the preparation; and a method of wound healing which comprises the step of covering the wound of a subject with the wound-covering material to protect the wound.

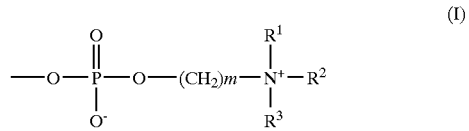

(I)

15 Claims, 5 Drawing Sheets

(1 of 5 Drawing Sheet(s) Filed in Color)

U.S. PATENT DOCUMENTS 5,977,257 A * 11/1999 Waki et al. .................. 525/131
6,204,324 B1 * 3/2001 Shuto et al. ................. 524/807

FOREIGN PATENT DOCUMENTS

| JP | 07-247355 | 9/1995 |
| JP | 08-333421 | 12/1996 |
| JP | 09-003132 | 1/1997 |
| JP | 09-241330 | 9/1997 |
| JP | 09-315949 | 12/1997 |
| JP | 10045626 A1 | 2/1998 |
| JP | 10-139789 | 5/1998 |
| WO | WO-94/14897 A1 | 7/1994 |
| WO | WO-98/22162 A1 | 5/1998 |

OTHER PUBLICATIONS

K.M. Defife, et al., "Adhesion and cytokine production by monocytes on poly(2–methacryloyloxyethyl phosphorylcholine–co–alkyl methacrylate)–coated polymers", Journal of Biomedical Materials Research, Apr. 1995, vol. 29, No. 4, Apr. 1995, p. 431–439.

* cited by examiner

WOUND-COVERING PREPARATION, WOUND-COVERING MATERIAL, AND METHOD OF WOUND HEALING

TECHNICAL FIELD

The present invention relates to a wound covering agent, a wound covering material and a wound treatment method. More specifically, it relates to a wound covering agent and wound covering material which are effective for cleaning wound sites and removing necrotic tissue and which have excellent hydrophilicity and biocompatibility, and to a wound treatment method employing the wound covering material. According to the present invention, it is possible to alleviate pain by wiping or covering wounds, ulcer or burn injury sites with the wound covering material, and to treat sites of skin loss due to wounds or burn injury by accelerating re-epithelialization and granulation. It is also effective for improving the quality of life (QOL) after healing by preventing secondary infection and preventing scar and contracture formation caused by prolonged inflammation.

BACKGROUND ART

Management methods for wounds and diseases such as traumatic wounds, dermatomic wounds and the like are largely classified as either dry dressing in which the wounded site is left open or is protected with gauze to positively maintain a dry condition, or wet dressing, which involves covering it with a urethane film or the like with low moisture permeability.

The former method is aimed at positively promoting crust formation to reduce external bacterial infection and prevent loss of body moisture; however, it is known that drying of the wound surface delays re-epithelialization and that adhered crust peels off when the covering material is exchanged, thus injuring the wound surface and prolonging the healing time.

The latter method occludes the wound site to prevent infection before it can occur and to hasten wound healing by providing an appropriate moist environment. With exudative wounds, however, accumulating wound fluid can be reabsorbed on the wound surface causing reinfection, and therefore a hydrophilic fibrous material is used in combination to control excess exudate.

Ointment therapy with antibiotics is also employed with lint cloths or gauze against the risk of infection with wide-area burn injury or third degree burns. However, neo-granulated tissue penetrates the fiber structure as it develops, and this is associated with problems in that delayed wound healing occurs accompanied with injury of granulation when the wound covering is exchanged. Japanese Patent Laid-open Publications No. SHO 51-56040 and No. SHO 63-51865 disclose non-sticky wound covering materials, but they do not always provide fully satisfactory results.

According to Japanese Patent Public Inspection No. HEI 7-504459, there is disclosed a wound covering material which is one of working examples of a polymer composition comprising a polymer having a zwitterionic pendant group with another polymer having desirable mechanical and/or physical properties; however, no specific polymer composition components or wound coverings are provided.

DISCLOSURE OF THE INVENTION

It is an object of the present invention to provide a wound covering material that has high biocompatibility, is safe and has low skin irritation, and that accomplishes proper healing of wounds without adhesion of crustation or granulation to the wound covering material, as well as a wound covering agent that can be used to produce such a wound covering material.

It is another object of the present invention to provide a wound treatment method that accomplishes proper healing of wounds in a safe manner without irritation to the skin.

As a result of searching for wound covering materials with excellent biocompatibility in order to solve the aforementioned problems, the present inventors found out that a specific polymer with a group related to the polar group of a phospholipid (phosphatidylcholine), which is a major component of biological membranes, is stable, and has a moisture retaining effect and a function that accelerates wound healing, to complete the present invention.

That is, the present invention provides a wound covering agent comprising a polymer having a group represented by the following formula (I):

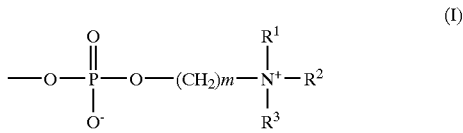

where $R^1$, $R^2$ and $R^3$ are the same or different and each represents a hydrogen atom or an alkyl group having 1 to 4 carbon atoms, and m represents an integer of 2–4.

The present invention further provides the aforementioned wound covering agent wherein the polymer is selected from the group consisting of a homopolymer of monomer (a) having a group represented by formula (I) above, a copolymer of monomer (a) having a group represented by formula (I) above and another monomer (b), a crosslinked polymer thereof, and mixtures thereof.

The present invention still further provides the aforementioned wound covering agent wherein the monomer (a) is a monomer represented by the following formula (II):

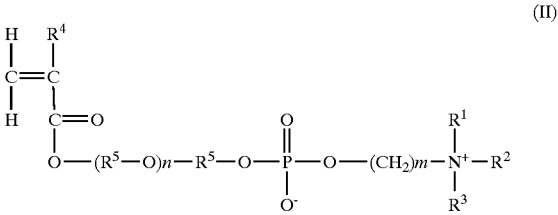

where $R^1$, $R^2$, $R^3$ and m are the same as in formula (I), $R^4$ represents a hydrogen atom, methyl group or —$CH_2$—COOH, $R^5$ represents an alkylene group having 2 to 10 carbon atoms and n represents an integer of 0–10.

The present invention still further provides the aforementioned wound covering agent wherein the monomer (a) is 2-methacryloyloxyethyl phosphorylcholine represented by the following formula (III):

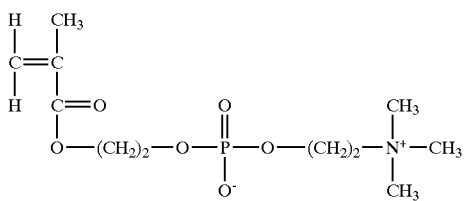

The present invention still further provides the aforementioned wound covering agent wherein the polymer is selected from the group consisting of a copolymer of the aforementioned monomer (a) and monomer (b), a crosslinked polymer thereof and mixtures thereof, and the monomer (b) is selected from the group consisting of monofunctional monomers, crosslinkable monomers and mixtures thereof.

The invention still further provides the aforementioned wound covering agent wherein the polymer comprises a unit represented by the following formula (IV):

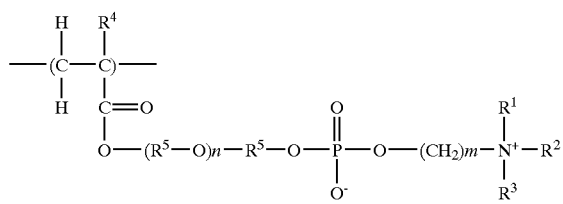

where $R^1$, $R^2$, $R^3$ and m are the same as in formula (I), $R^4$ represents a hydrogen atom, methyl group or —$CH_2$—COOH, $R^5$ represents an alkylene group having 2 to 10 carbon atoms and n represents an integer of 0–10.

The present invention still further provides the aforementioned wound covering agent wherein the polymer also comprises a unit represented by the following formula (V):

where $R^6$ represents a hydrogen atom, methyl group or —$CH_2$—COOH, $R^7$ represents a hydrogen atom, a carboxyl group or an alkoxycarbonyl group having 2 to 6 carbon atoms and X represents the group —Y—$Z^1$, a crosslink represented by —Y—$Z^2$—Y— or a crosslink represented by

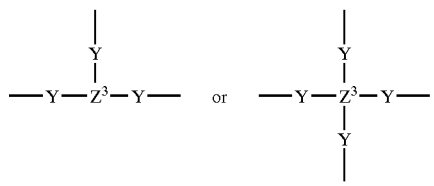

where Y represents —COO—, —CONH—, -o$C_6H_4$—, -m$C_6H_4$—, -p$C_6H_4$—, —OCO— or a dimethoxysilyl group; $Z^1$ represents a hydrogen atom, a sodium atom, a cyano group, a vinyl group, a glycidyl group, an alkyl group having 1 to 4 carbon atoms, a hydroxyalkyl group having 2 to 4 carbon atoms, a dihydroxyalkyl group having 2 to 4 carbon atoms, a pyrrolidonyl group, a sulfonic acid group, a sodium sulfonate group, 2-ethylhexyl group, trimethoxysilylpropyl group, triethoxysilylpropyl group, methyldimethoxysilylpropyl group, an oxyalkyl group having 2 to 6 carbon atoms or a 2–20mer group that is made of oxyalkylene groups each having 2 to 6 carbon atoms and that has a hydrogen atom or methyl group at terminal thereof; $Z^2$ represents —(AO)$_r$—A— where A is an alkylene group having 1 to 12 carbon atoms and r is an integer of 0–20; and $Z^3$ represents a trivalent or tetravalent hydrocarbon group having 3 to 12 carbon atoms, and wherein the proportion of units represented by formula (V) of the total of the number of units represented by formula (IV) and the number of units represented by formula (V) in the polymer is in a range of larger than 0% and no greater than 99%, and the number average molecular weight thereof is 5,000–1,000,000.

The present invention still further provides a wound covering material comprising the wound covering agent.

The present invention still further provides a wound treatment method that comprises a step of covering the wound site of a subject with the wound covering material to protect the wound site.

BRIEF DESCRIPTION OF THE DRAWINGS

The patent or application file contains at least one drawing executed in color. Copies of this patent or patent application publication with color drawing(s) will be provided by the office upon request and payment of the necessary fee.

PREFERRED EMBODIMENT OF THE INVENTION

Figure 1:
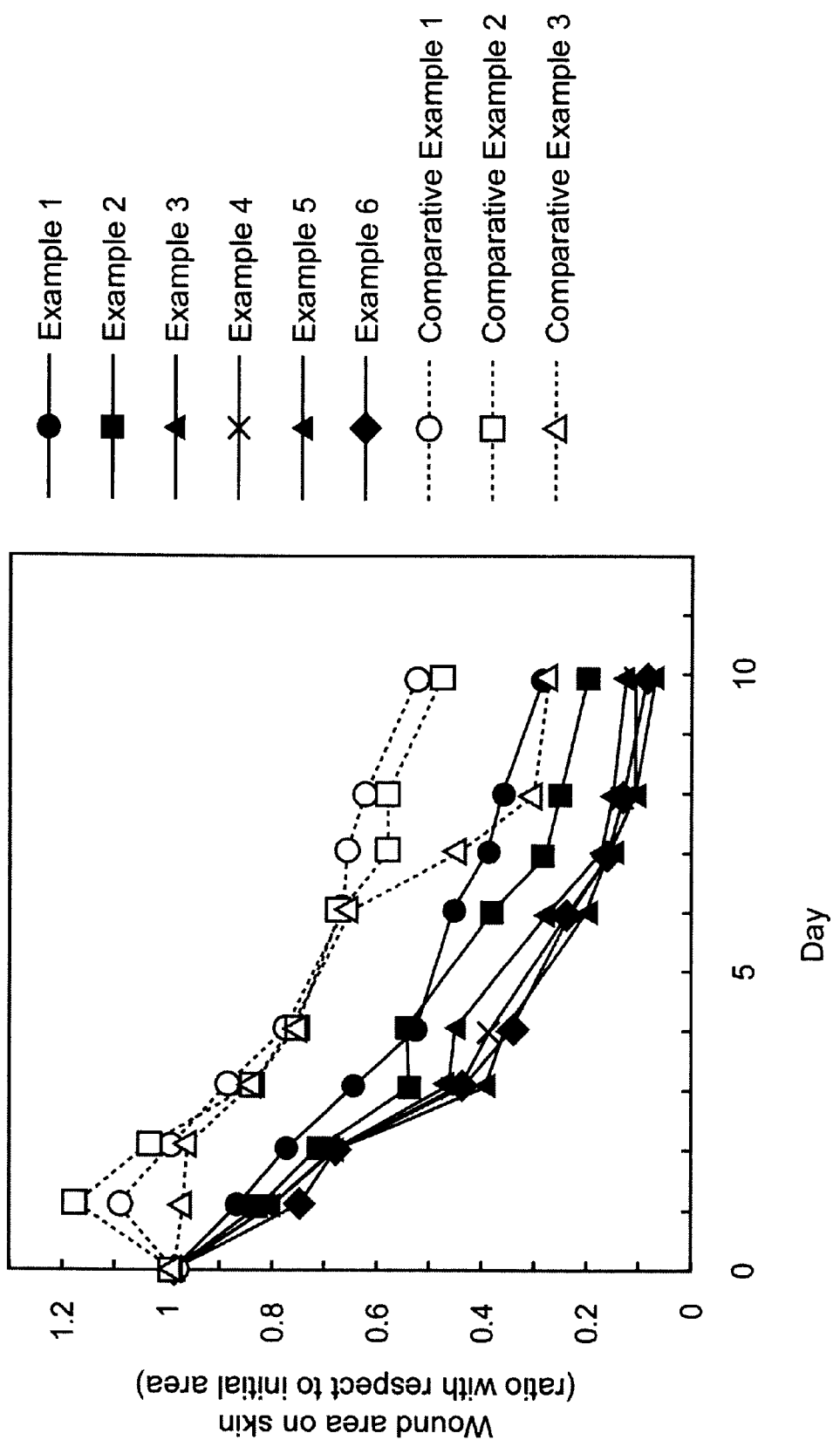
FIG. 1 is a graph showing the results of wound surface area measurement for Examples 1–6 and Comparative Examples 1–3.

The wound covering agent of the present invention includes a polymer with a phosphorylcholine-related group represented by formula (I) above (hereunder referred to as Polymer (I)).

In formula (I), $R^1$, $R^2$ and $R^3$ are the same or different and each represents a hydrogen atom or an alkyl group having 1 to 4 carbon atoms, and m represents an integer of 2–4.

Polymer (I) may be a homopolymer of a monomer having a group represented by the aforementioned formula (I) (hereunder a referred to as monomer (a)), a copolymer of monomer (a) and another monomer (hereunder referred to as monomer (b)), a crosslinked polymer thereof or mixtures thereof.

The aforementioned monomer (a) is preferably a monomer represented by formula (II) above.

In formula (II), $R^1$, $R^2$, $R^3$ and m are the same as in formula (I), $R^4$ represents a hydrogen group, methyl group or —CH$_2$—COOH, R$^5$ represents an alkylene group having 2 to 10 carbon atoms and n represents an integer of 0–10.

As specific examples of monomer (a) there may be mentioned 2-(meth)acryloyloxyethyl-2'-(trimethylammonio)ethyl phosphate, 3-(meth)acryloyloxypropyl-2'-(trimethylammonio)ethyl phosphate, 4-(meth)acryloyloxybutyl-2'-(trimethylammonio)ethyl phosphate, 5-(meth)acryloyloxypentyl-2'-(trimethylammonio)ethyl phosphate, 6-(meth)acryloyloxyhexyl-2'-(trimethylammonio)ethyl phosphate, 2-(meth)acryloyloxyethyl-2'-(triethylammonio)ethyl phosphate, 2-(meth)acryloyloxyethyl-2'-(tripropylammonio)ethyl phosphate, 2-(meth)acryloyloxyethyl-2'-(tributylammonio)ethyl phosphate, 2-(meth)acryloyloxypropyl-2'-(trimethylammonio)ethyl phosphate, 2-(meth)acryloyloxybutyl-2'-(trimethylammonio)ethyl phosphate, 2-(meth)acryloyloxypentyl-2'-(trimethylanmmonio)ethyl phosphate, 2-(meth)acryloyloxyhexyl-2'-(trimethylammonio)ethyl phosphate, 2-(meth)acryloyloxyethyl-3'-(trimethylammonio)propyl phosphate, 3-(meth)acryloyloxypropyl-3'-(trimethylammonio)propyl phosphate, 4-(meth)acryloyloxybutyl-3'-(trimethylammonio)propyl phosphate, 5-(meth)acryloyloxypentyl-3'-(trimethylammonio)propyl phosphate, 6-(meth)acryloyloxyhexyl-3'-(trimethylammonio)propyl phosphate, 2-(meth)acryloyloxyethyl-4'-(trimethylammonio)butyl phosphate, 3-(meth)acryloyloxypropyl-4'-(trimethylammonio)butyl phosphate, 4-(meth)acryloyloxybutyl-4'-(trimethylammonio)butyl phosphate, 5-(meth)acryloyloxypentyl-4'-(trimethylammonio)butyl phosphate and 6-(meth)acryloyloxyhexyl-4'-(trimethylammonio)butylphosphate. Here, "(meth)acryl" means methacryl and/or acryl.

Particularly preferred for monomer (a) is 2-methacryloyloxyethyl phosphorylcholine (hereunder referred to as MPC).

The proportion of units based on monomer (a) in Polymer (I) is preferably in a range of 20–80 mol %, and more preferably 30–70 mol %, as the proportion with respect to the total units.

Monomer (b), i.e. the monomer other than monomer (a) composing Polymer (I), is not particularly restricted and may be any monofunctional monomer and/or crosslinkable monomer that can be polymerized with monomer (a). When a crosslinkable monomer is used, crosslinking within the molecules of Polymer (I) or crosslinking between Polymer (I) and other materials can easily formed, to obtain a Polymer (I) as a crosslinked polymer.

As specific examples for the monofunctional monomer there may be mentioned hydrophilic monomers such as (meth)acrylic acid, sodium(meth)acrylate, 2-hydroxyethyl (meth)acrylate, glycerol(meth)acrylate, N-vinylpyrrolidone, acrylonitrile, (meth)acrylamide, polyethyleneglycol mono (meth)acrylate, vinylbenzenesulfonic acid, sodium vinylbenzenesulfonate, itaconic acid, sodium itaconate, maleic acid, sodium maleate, fumaric acid and sodium fumarate, and hydrophobic monomers such as methyl(meth) acrylate, ethyl(meth)acrylate, butyl(meth)acrylate, lauryl (meth)acrylate, dodecyl(meth)acrylate, stearyl(meth) acrylate, 2-ethylhexyl(meth)acrylate, styrene, vinyl acetate, and mixtures thereof.

As crosslinkable monomers there may be mentioned monomers with two or more polymerizable functional groups, and/or monomers with one or more crosslinking reactive functional groups and one or more polymerizable functional groups. As specific examples of monomers with two or more polymerizable functional groups there may be mentioned ethyleneglycol di(meth)acrylate, diethyleneglycol di(meth)acrylate, triethyleneglycol di(meth)acrylate, tetraethyleneglycol di(meth)acrylate, polyethyleneglycol di(meth)acrylate, propyleneglycol di(meth)acrylate, polypropyleneglycol di(meth)acrylate, 1,4-butanediol di(meth)acrylate, glycerol di(meth)acrylate, trimethylolpropane tri(meth)acrylate, cyclohexanediol di(meth)acrylate, divinylbenzene, divinylglycol, and mixtures thereof.

As monomers with one or more crosslinking reactive functional groups and one or more polymerizable functional groups there may be mentioned monomers having, in addition to a polymerizable functional group, a crosslinking reactive functional group which is a functional group that can form a crosslink with another portion of Polymer (I) or with the base material described below, either by the functional group alone or in combination with a crosslinking agent. Specifically there may be mentioned monomers with silane groups, for example, alkyloxysilane groups such as (3-methacryloyloxypropyl)trimethoxysilane, (3-methacryloyloxypropyl)triethoxysilane, (3-methacryloyloxypropyl)methyldimethoxysilane and trimethoxyvinylsilane; monomers with siloxane groups; monomers with glycidyl groups such as glycidyl methacrylate; monomers with amino groups such as allylamine, aminoethyl (meth)acrylate and 2-methylallylamine; monomers with groups such as carboxyl, hydroxyl, aldehyde, thiol, halogen, methoxy, epoxy, succinimide and maleimide groups; and mixtures thereof.

As crosslinking agents that can form crosslinks with crosslinking reactive functional groups there may be mentioned, for example, dialdehydes such as glutaraldehyde, succinimides and maleimides such as disuccinimidyl glutarate (DSG), dithiobis-succinimidyl propionate (DSP), disuccinimidyl suberate (DSS), disuccinimidyl tartrate (DST), ethyleneglycol bis-succinimidyl succinate (EDS), maleimide butyryloxysuccinimide ester (GMBS), maleimide benzoylhydroxysuccinimide ester (MBS) and succinimidylmaleimide phenylbutryate (SMPB), and compounds that can form ion complexes with polyvalent metal ions, such as polyfunctional acid chlorides such as dicarboxylic acid chlorides, polyfunctional diisocyanates such as diisothiocyanostilbene disulfonic acid, imide esters such as dimethyl suberate, polyfunctional amines, pyridyl disulfides such as dipyridyldithiopropionamide butane (DPDPB), nitroaryl halides such as fluoronitrophenyl azide, polyfunctional alcohols, polyfunctional carboxylic acids, active halogens, diazoalkanes, and sulfonic acid.

Monomer (b) is preferably a monofunctional or polyfunctional monomer that can provide a unit represented by formula (V) described below.

Monomers other than these are preferably radical polymerizable monomers. The other monomers may be used alone or as mixtures of two or more.

Polymer (I) is preferably a copolymer including a hydrophobic monomer as monomer (b). Specifically, the proportion of units composed of the hydrophobic monomer in Polymer (I) is preferably at least 20 wt %. Polymer (I) containing the hydrophobic monomer in such a manner is preferred because this can provide a wound covering agent that is hardly soluble in water so that a stable shape can be maintained for various forms of wound covering materials in which the wound covering agent is used, and to prevent the wound covering agent from being washed off from the affected area.

Polymer (I) preferably includes a unit represented by formula (IV) above (hereunder referred to as unit (IV)).

In formula (IV), $R^1$, $R^2$, $R^3$ and m are the same as in formula (I), and $R^4$, $R^5$ and n are the same as in formula (II).

The proportion of unit (IV) in Polymer (I) is preferably in a range of 20–80 mol %, and more preferably 30–70 mol %, as the proportion with respect to the total units.

Polymer (I) also preferably includes a unit represented by formula (V) above (hereunder referred to as unit (V)).

In formula (V), $R^6$ represents a hydrogen atom, methyl group or —$CH_2$—COOH, $R^7$ represents a hydrogen atom, a carboxyl group or an alkoxycarbonyl group having 2 to 6 carbon atoms, and X represents a group represented by —Y—$Z^1$, a crosslink represented by —Y—$Z^2$—Y— or a crosslink represented by

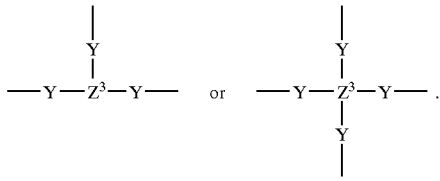

These crosslinks may be crosslinks within Polymer (I), or they may be crosslinks between Polymer (I) and another material. specifically, when the crosslinks are crosslinks within Polymer (I), Polymer (I) may have divalent to tetravalent crosslinks connecting two to four units (V) in Polymer (I). When the crosslinks are crosslinks between Polymer (I) and another material, Polymer (I) may have crosslinks connecting one or more units (V) with one or more sites in the other material. These crosslinks may be bonds to the carbon atom to which group $R^6$ of unit (V) is bonded, to crosslink unit (V).

Y represents —COO—, —CONH—, -$oC_6H_4$—, -$mC_6H_4$—, -$pC_6H_4$—, —OCO— or dimethoxysilyl group; $Z^1$ represents a hydrogen atom, a sodium atom, a cyano group, a vinyl group, a glycidyl group, an alkyl group having 1 to 4 carbon atoms, a hydroxyalkyl group having 2 to 4 carbon atoms, a dihydroxyalkyl group having 2 to 4 carbon atoms, a pyrrolidonyl group, a sulfonic acid group, a sodium sulfonate group, 2-ethylhexyl group, trimethoxysilylpropyl group, triethoxysilylpropyl group, methyldimethoxysilylpropyl group, an oxyalkyl group having 2 to 6 carbon atoms or a 2–20mer group that is made of oxyalkylene groups each having 2 to 6 carbon atoms and that has a hydrogen atom or methyl group at the end; $Z^2$ represents —$(AO)_r$—A— where A is an alkylene group having 1 to 12 carbon atoms and r is an integer of 0–20; and $Z^3$ represents a trivalent or tetravalent hydrocarbon group having 3 to 12 carbon atoms.

Particularly preferred for unit (V) are those groups in which X is —Y—$Z^1$, where Y is —COO— and $Z^1$ is an alkyl group having 1 to 4 carbon atoms.

When Polymer (I) includes unit (IV) and unit (V), their proportion, as the proportion of the number of units (V) of the total of the number of units (IV) and the number of units (V), is preferably in a range of larger than 0% and no greater than 99%.

The molecular weight of Polymer (I) is not particularly restricted, but the number average molecular weight is preferably 5,000–1,000,000.

Polymer (I) maybe produced by any publicly known process. Specifically it may be produced, for example, by polymerizing a starting material containing monomer (a) and if necessary monomer (b) by publicly known methods such as methods employing polymerization initiator, heating, light, radiation or a combination thereof, and forming crosslinks if necessary. The crosslink formation may be accomplished at the same time or after the polymerization reaction, and if necessary the crosslinking agent may be added before or after the polymerization reaction.

The proportion of monomer (a) in the starting material may be in a range of 20–80 mol %, and more preferably 30–70 mol %, with respect to the total units.

When Polymer (I) is a copolymer of monomer (a) and monomer (b), the proportions of monomer (a) and monomer (b) for the copolymerization are preferably such that the proportion of monomer (b) is larger than 0 mol % and no greater than 99 mol % of the total of monomer (a) and monomer (b).

Monomer (a) may be produced by the publicly known processes disclosed in Japanese Patent Publication No. SHO 60-21599, Japanese Patent Publication No. HEI 2-49316, Japanese Patent Laid-open Publication No. SHO 63-222183, Japanese Patent Laid-open Publication No. HEI 5-107511, Japanese Patent Laid-open Publication No. HEI 6-41157, WO93/01121, WO97/08177, etc. Alternatively, 2-methacryloyloxyethyl phosphorylcholine may be obtained by reacting 2-bromoethylphosphoryl dichloride, 2-hydroxyethylphosphoryl dichloride and 2-hydroxyethyl methacrylate to obtain 2-methacryloyloxyethyl-2'-bromoethylphosphoric acid, and further reacting this with trimethylamine in methanol (Kobunshi Ronbunshu, Vol.35, p.423–427, 1978; Polymer Journal, Vol.22, No.5).

The wound covering material of the present invention contains the aforementioned wound covering agent of the present invention.

The wound covering material of the present invention may contain, in addition to the aforementioned wound covering agent of the present invention, other components such as base materials, hydrophobic high molecular substances, ointment bases, antibacterial disinfectants, antibiotics, growth factors, crude drugs, plant extracts and the like, depending on the form.

As base materials there may be mentioned gauzes, nonwoven fabrics, films, sheets and foam materials made of polyurethane, nylon, polyester, acryl, polyethylene, cupra, rayon, silicon, cotton and the like. In particular, by using a base material having a crosslinkable functional group such as an amino group, carboxyl group, hydroxyl group, aldehyde group or epoxy group, it is possible to form crosslinks with the wound covering agent. More specifically, for example, there may be mentioned base materials wherein cellulose including functional group-containing polymers is ring-opened to form aldehyde groups, and base materials wherein a urethane material has been hydrolyzed to form amino groups. As hydrophobic high molecular substances there may be mentioned polyisobutylene which exhibits plasticity and styrene-isoprene-styrene block copolymer which exhibits elasticity. As ointment bases there may be mentioned oil bases, hydrophilic bases, emulsifiers and mixtures thereof. Oil bases that may be used are not particularly restricted so long as they are oil components that are commonly employed as ointments, and as preferred ones there may be mentioned fats and oils, waxes, higher fatty acids, hydrocarbons, higher alcohols, esters, purified oils, silicone oils and the like. As water-soluble bases there may be mentioned glycolic acids and higher alcohols. As emulsifiers there may be used any desired emulsifiers so long as the effect of the invention is not hindered, and these include glycerin fatty acid esters, propyleneglycol fatty acid esters, sorbitan fatty acid esters, polyoxyethylenesorbitan fatty acid esters, polyoxyethylenesorbit tetraoleate, polyoxyethylene alkyl ether, polyoxyethylene polyoxypropylene alkyl ether, polyethyleneglycol glycol fatty acid esters, polyglycerin fatty acid esters, lauryl fatty acid esters, sodium cetylsulfate, sodium polyoxyethylenelauryl sulfate, carboxybetaines, aminocarboxylic acids, sulfobetaines, and the like. As antibacterial disinfectants there may be mentioned sulfa agents such as acrinol, povidone-iodine and silver sulfadiazine. As antibiotics there may be mentioned macrolide-based antibiotics such as erythromycin, tetracycline-based antibiotics such as tetracycline, aminoglycoside-based antibiotics such as kanamycin, new quinolone-based antibiotics such as nadifloxacin, polypeptide antibiotics such as polymixine, and fungus treatment agents such as griseofulvin and amphoterin B. As growth factors there may be mentioned EGF (epithelial growth factor), TGF (transforming growth factor), NGF (neural growth factor), IGF (insulin-like growth factor), VEGF (vascular epithelial growth factor), FGF (fibroblast growth factor), LPA (lysophosphatidic acid), sphingosine monophosphate and the like. As crude drugs there may be mentioned rosskastanien extract and the like. As plant extracts there may be mentioned aloe extract and the like.

The process for producing the wound covering material of the invention is not particularly restricted, and it may be produced by obtaining Polymer (I) and giving the polymer a desired shape, optionally followed by further treatments such as crosslinking reaction and mixing with other materials. The wound covering material may also be produced by giving monomer (a) or a monomer composition containing monomer (a) a desired shape of, e.g., film or sheet, and polymerizing the monomer composition, optionally followed by further treatments such as crosslinking reaction and mixing with other materials. The crosslinking reaction may optionally be carried out by adding one of the aforementioned crosslinking agents, and subjecting the reaction system to heat, light or radiation, or adding a solution or vapor containing another component that promotes crosslinking reaction.

The wound covering material of the invention may be in the form of a hydrocolloid composition, a gel, particles, a paste, a film, a sheet or a foam material, or in the form in which the wound covering agent is adhered to any of the base materials mentioned above.

Preferred hydrocolloid compositions are those compounding polymer (I) and the hydrophobic high molecular substance at a weight ratio in a range of 30:70–70:30, and molded into a sheet form.

When a wound covering material according to the present invention which is in the form of a hydrocolloid composition is applied to a wound, it is possible to prevent maceration of healthy skin surrounding the wound, to promote tissue regeneration by maintaining a suitable moist environment due to absorption of the exudate in the wound, to maintain a low oxygen partial pressure to promote neovascularization, and to maintain an acidic pH in the wound to inhibit bacterial proliferation and promote decomposition of necrotic tissue, thus preventing infection from the outside.

The gel preferably contains polymer (I) in an amount of at least 10 wt %, as the proportion of units based on monomer (a) with respect to the total dry weight of the gel. If the proportion of units derived from monomer (a) is at least 10 wt %, it will be possible to adequately exhibit the effect of the phosphorylcholine-related groups represented by formula (I).

The gel may be in the form of a mass, particles, a sheet or the like.

A massive gel can be obtained by polymerizing and crosslinking the monomer composition containing monomer (a) and the monomer having crosslinking ability.

A particulate gel can be obtained by a method in which a massive gel such as described above is pulverized, or a method in which the monomer composition containing monomer (a) and the monomer having crosslinking ability is subjected to suspension polymerization in a solvent in which the monomer composition is insoluble, such as hexane, and the resulting fine particles are swelled in water.

A sheet-like gel can be obtained by a method in which a massive gel such as described above is cut out into a sheet, a method in which a particulate gel such as described above is molded into a sheet, or a method in which a copolymer sheet formed by a solvent casting process or melt press process is swelled with water. The sheet-like gel can be rendered as a more stable sheet-like gel by adding thereto a water-soluble polymer such as polyvinyl alcohol, polyethylene glycol, polyvinylpyrrolidone or the like during the molding. By using a sheet-like gel that contains units derived from the hydrophobic monomer preferably at 20 wt % or more, it is possible to easily obtain a gel sheet-like wound covering material that is hardly soluble in water.

The particles preferably contain polymer (I) in an amount of at least 10 wt % in terms of the proportion of units derived from monomer (a) with respect to the total dry weight of the particles.

The aforementioned particles can be obtained by a method in which a massive gel is pulverized, or a method in which the monomer composition containing monomer (a) and the monomer having crosslinking ability is subjected to suspension polymerization in a solvent in which the monomer composition is insoluble, such as hexane.

The aforementioned paste can be obtained by adding polymer (I) in an amount of 5–99 wt %, and preferably 10–90 wt %, to any of the ointment bases mentioned above.

When a wound covering material according to the present invention in the form of a hydrocolloid composition, gel, particles or paste is applied to an affected area, its form may be freely altered depending on the manner of wound in order to exhibit an adequate effect of closing off the wound from the outside while maintaining suitable moisture, alleviating pain caused by irritation from the outside, and reducing the risk of secondary infection from the outside.

The aforementioned film or sheet can be obtained by a method in which, after polymer (I) is obtained, it is molded into a film or sheet and further processed if necessary by crosslinking reaction or the like, or a method in which the monomer including monomer (a) is spread into a film or sheet form and then polymerized to make a film or sheet polymer and further processed if necessary by crosslinking reaction or the like.

The wound covering material of the present invention may include a base material and the aforementioned wound covering agent adhered to the base material. This type of wound covering material can be obtained, for example, by a method in which a liquid including polymer (I), and if necessary a crosslinking agent or the like, is adhered to abase material such as described above and then if necessary further processed by drying, crosslinking, etc., or a method in which, after adhereing a liquid including monomer (a), and if necessary monomer (b) and a crosslinking agent or the like, to the base material, polymerization is carried out and if necessary further processing such as drying, crosslinking, etc. is carried out. The adhesion of the liquid may be impregnation or coating onto the base material, or sandwiching a sheet-like base that has been impregnated therewith between two sheets. The crosslinks formed by the crosslinking reaction may be crosslinks within the polymer and/or crosslinks between the polymer and base material.

More specifically, a wound covering material may be obtained, for example, by a method in which a monomer composition including monomer (a) and a hydrophobic monomer is copolymerized to obtain a hardly water-soluble copolymer which is then dissolved in a solvent and impregnated into the base material, a method in which a composition including monomer (a) and a crosslinking agent is dissolved in a solvent to obtain a solution which is then impregnated into a sheet-like base material prior to polymerization, or a method in which a copolymer obtained by copolymerizing monomer (a) and a monomer having crosslinking ability is impregnated into a sheet-like base material and then crosslinked.

When a wound is treated with a wound covering material of the present invention in the form of a film, sheet or foam material, or a wound covering material of the present invention in the form in which a wound covering agent is adhered to a base material in the form of a gauze, nonwoven fabric, film, sheet or foam material, it is possible to prevent maceration of healthy skin surrounding the wound, to promote tissue regeneration by maintaining a suitable moist environment due to absorption of the exudate in the wound, to maintain a low oxygen partial pressure to promote neovascularization, and to maintain an acidic pH in the wound to inhibit bacterial proliferation and promote decomposition of necrotic tissue, thus preventing infection from the outside.

The wound treatment method of the present invention includes a step of protecting a wound site of a subject by covering the wound site with a wound covering material according to the invention.

The subject may be a human or an animal other than a human, such as a domestic animal or pet. As examples of animals other than humans there may be mentioned horses, cows, pigs, mules, sheep, chickens, dogs, cats, monkeys, mice, guinea pigs, squirrels, small birds, weasels, raccoons, skunks, and other various mammals and birds.

The types of wounds to be treated by the wound treatment method of the present invention are not particularly limited, and include various kinds of wounds such as surgical wounds, injury wounds, full-thickness wounds and burn wounds, as well as wounds arising from various types of ulcers, such as skin ulcers, corneal ulcers, arterial obstructive crural ulcers, continuous pressure-induced decubital and diabetic ulcers, burn ulcers, injury ulcers, radiation ulcers, drug-induced ulcers, post-operative ulcers, inflammatory ulcers, simple ulcers and other types of angiopathic ulcers, chronic (intractable) ulcers, and the like.

The step of protecting the wound site of a subject by covering the wound site with the aforementioned wound covering material is not particularly limited, and it may be carried out by simply placing the wound covering material by itself so as to cover the wound site of the subject, or by placing the wound covering material between a medical instrument and the wound site. As specific examples of medical instruments there may be mentioned pouches, catheters, tubes, cannula and plaster.

When applied to a subject, the wound covering agent, wound covering material or wound treatment method of the present invention exhibit high affinity for the wound surface and low anchorage to skin components such as crust or granules in the wound, and therefore accelerate rapid wound healing.

The bioaffinity and resistance to crust formation and granulation of the wound covering agent, wound covering material and wound treatment method of the present invention can be confirmed by an in vitro experimental system for a toxicity test, extracellular matrix production test or cell migration test using cultured cells, an adhesion test or chemokine test using whole blood, platelet rich plasma, rinsed platelets or granulocytes, lymphocytes or monocytes, or an experimental system suited for an adsorption test using fibrinogen, fibrin or other proteins, a clotting factor activation test, an extracellular matrix adhesion test using fibronectin or collagen, or another type of anchoring test on blood clotting components and granulation tissue. It is understood that the results of a crust adhesion test show that coatings for the wound covering material of the present invention can prevent anchoring of the blood clotting components.

The treatment-accelerating effect of the wound covering agent, wound covering material and wound treatment method of the present invention can be confirmed using a model for various wounds, skin ulcers, corneal ulcers, various kinds of surgical wounds, injury wounds, arterial obstructive crural ulcers, continuous pressure irritation-induced decubital and diabetic ulcers, burn ulcers, injury ulcers, radiation ulcers, drug-induced ulcers, post-operative ulcers, inflammatory ulcers, simple ulcers, etc., and an experimental system appropriate for evaluating the treatment progress of full-thickness wound conditions, and especially skin ulcers treatment or prophylactic activity, or the accelerating activity on skin treatment and healing. The results of effect-confirmation tests in experimental surgical wound animal models in the examples and comparative examples provided below demonstrate that the examples which employed wound covering materials according to the present invention had an effect of accelerating wound healing compared to the comparative examples. In the examples, no crust adhesion was found, the number of days to complete healing was shortened, and a notable improvement was seen in visual observations including the color tone in and around the affected areas, as compared to the comparative examples. The particularly distinguishing aspects were accelerated re-epithelialization of full-thickness wounds, granulation tissue formation and neovascularization, which are all factors in wound healing, and therefore faster repair of the affected sites and relative inconspicuousness of cicatrization caused by the medical treatment. This effect can be utilized to minimize general surgical scars and injury scars, and it was judged to be highly useful from the standpoint of esthetic effect which is an important element of QOL. No visually discernible side-effects were seen at sites to which the wound covering materials of the present invention were applied.

The effect of the wound covering agent, wound covering material and wound treatment method of the present invention on preventing keroid or hypertrophic scar and contracture may be confirmed by immunostaining of infiltration of wound contraction-governing myofibroblasts with anti α-SM-actin antibodies in such animal experiments as described above, by the appearance of multinucleated giant cells which play a major role in recognition reaction against foreign body, on the surface of subcutaneously implanted wound covering materials, or based on the presence or absence of adhesion of macrophages from which multinucleated giant cells are derived, on the surface of the wound covering agent. Since the appearance of contraction-implicated myofibroblasts was suppressed in the examples provided below, the wound covering materials of the present invention were judged to have excellent performance.

Thus, the wound covering material of the present invention has a treating effect and a symptom ameliorating effect on angiopathic ulcers typical of which are arterial obstructive crural ulcers and phlebostatic crural ulcers, of difficult-to-treat chronic (intractable) skin ulcers such as continuous pressure irritation-induced decubital and diabetic ulcers that are attributed to age, dietary and physical factors, of burn ulcers, injury ulcers, radiation ulcers, drug-induced ulcers, post-operative ulcers, inflammatory ulcers, simple ulcers and the like categorized according to their various causes, and of full-thickness wounds and burn wounds that often are accompanied by secondary infection; it was also judged to be excellent from the standpoint of improved prognosis for keroid or hypertrophic scar or wound scars.

The wound covering agent of the present invention has a treating effect and an ameliorating effect on the aforementioned ulcers as well as symptoms of full-thickness wounds and burn wounds that often induces infection, and is also useful for preventing keroid and hyperplastic cicatrization and as a prophylactic covering agent against injury wounds.

The wound treatment method of the present invention is advantageous from the standpoint of accelerating healing and improving prognosis, as a method allowing treatment of wounds such as the aforementioned ulcer types and full-thickness wounds and burn wounds, without anchorage or foreign body reaction between the wound and the covering material.

EXAMPLES

The present invention will now be explained in further detail by way of examples which, however, are in no way intended to restrict the invention.

Example 1

A 0.5% ethanol solution of a copolymer composed of MPC and butyl methacrylate (hereunder abbreviated to "BMA") (containing 30 mol % MPC; weight average molecular weight: approximately 480,000) was prepared. A nonwoven fabric (lint fabric manufactured by Hakujuji, K.K.) was immersed in this solution, and after adequate soaking in the solution, it was dried for 12 hours at room temperature. This procedure was repeated 3 times to obtain a polymer-coated lint fabric. The fabric was used for a full-thickness wound model experiment, taking visual observations and measuring the wound area. The results are shown in Table 1 and FIG. 1.

Example 2

26 g of MPC, 5.2 g of glycidyl methacrylate, 0.25 g of t-butyl peroxypivalate and 102 g of ethanol were charged in a 200 ml 4-necked flask. The reaction was stirred at ice temperature with nitrogen blowing for 30 minutes. The temperature was then increased to 50° C. for polymerization to obtain a copolymer in ethanol. The molecular weight of the obtained copolymer was 75,000 as evaluated by GPC based on polyethylene glycol as the reference. Japan Pharmacopoeia gauze was immersed in the copolymer solution for absorption of the solution, and then dried in a drier at 80° C. for 4 hours, subsequently heat treated at 110° C. for 4 hours and washed with water to obtain a polymer-coated gauze. This was used as a covering material in a full-thickness wound model experiment, noting the histopathological findings and measuring the wound area. The results are shown in Table 2 and FIG. 1.

Example 3

A 0.5% ethanol solution of a copolymer composed of MPC and 2-ethylhexyl methacrylate (containing 30 mol % MPC; weight average molecular weight: approximately 580,000) was prepared. A polyurethane foam material (Hydrocite, product of Smith & Nephew) was immersed therein and drawn out, and then dried at room temperature after absorbing out the excess solution with filter paper. This procedure was repeated twice to obtain a polymer-coated polyurethane foam. This was used as a covering material in a full-thickness wound model experiment, noting the histopathological findings and measuring the wound area. The results are shown in Table 2 and FIG. 1.

Example 4

A 0.5% ethanol solution of a copolymer composed of MPC and BMA (containing 30 mol % MPC; weight average molecular weight: approximately 480,000) was prepared. A polyurethane film (Biocclusive, product of Johnson & Johnson) was immersed in the solution and drawn out, and then dried at room temperature for 12 hours after absorbing out the excess solution with filter paper. This procedure was repeated twice to obtain a polymer-coated polyurethane film. This was used as a covering material in a full-thickness wound model experiment, taking visual observations and measuring the wound area. The results are shown in Table 1 and FIG. 1.

Example 5

A polymerization solution prepared by mixing 5 g of MPC, 0.5 g of ethyleneglycol dimethacrylate, 5 g of ethanol and 0.1 g of t-butyl peroxyneodecanoate at ice temperature was thinly spread out on a polypropylene petri dish with an 80 mm diameter, and polymerization was carried out in a drier at 50° C. for 4 hours. The resulting sheet was transferred to a mortar, and an equivalent weight of polyisobutylene (molecular weight: 2,800,000, product of Scientific Polymer Products) slab was slowly added and mixed therewith to obtain a hydrocolloid. This was used as a covering material in a full-thickness wound model experiment, noting the histopathological findings and measuring the wound area. The results are shown in Table 2 and FIG. 1.

Example 6

Six grams of a polymerization solution prepared by mixing 108 g of MPC, 12 g of polyethyleneglycol dimethacrylate (molecular weight: approximately 600), 280 g of water and 4 g of succinic peroxide at ice temperature was spread out on a polypropylene petri dish with a 47 mm diameter, and polymerization was carried out in a drier at 60° C. for 2 hours to yield a hydrogel in sheet form. This was used as a covering material in a full-thickness wound model experiment, noting the histopathological findings and measuring the wound area. The results are shown in Table 2 and FIG. 1.

Comparative Example 1

A nonwoven lint fabric (product of Hakujuji, K.K.) was used as a covering material a full-thickness wound model experiment, taking visual observations and measuring the wound area. The results are shown in Table 1 and FIG. 1.

Comparative Example 2

A pure cotton-woven base cloth was degreased and bleached to make Japan Pharmacopoeia gauze (Type 1, product of Hakujuji, K.K.) for use as a covering material in a full-thickness wound model experiment, noting the histopathological findings and measuring the wound area. The results are shown in Table 2 and FIG. 1.

Comparative Example 3

A polyurethane foam material (Hydrocite, product of Smith & Nephew) was used as a covering material in a full-thickness wound model experiment, noting the histopathological findings and measuring the wound area. The results are shown in Table 2 and FIG. 1.

Full-thickness Wound Model Experiment

Nine ddy mice per group (female, 6 weeks old, body weight: 25–30 g) were used as experimental animals. After shaving their hair under Nembutal anesthesia (30 mg/kg, intraabdominal administration) and disinfecting, a 1 cm-square template was placed against the skin on the dorsal midline to define an resection region on the skin, and a full-thickness wound was created with surgical scissors. The covering material was placed thereover immediately after creating the open wound. To ensure fixation of the covering material, the outer side was covered with an elastic bandage wound once around the torso. After creating the full-thickness wound, the covering was exchanged with a fresh covering once a day.

<Visual Observations>

A 4-level scale was used to evaluate the degree of bleeding on the wound surface when the used covering material was peeled off for exchange of the covering material. Table 1 shows the average values for 9 mice.

TABLE 1

Visual observations (bleeding) with covering material exchange

| Covering material | | Days after surgery | | | | | | |
|---|---|---|---|---|---|---|---|---|
| | | 1 | 2 | 3 | 4 | 5 | 6 | 8 |
| Example 1 | Polymer-lint fabric | 0.8 | 0.4 | 0.2 | 0.1 | 0.1 | 0.1 | 0 |
| Example 4 | Polymer-film | 0.1 | 0.1 | 0.1 | 0 | 0 | 0 | 0 |
| Comparative Example 1 | Lint fabric | 2.2 | 2.7 | 2.8 | 2.8 | 2.7 | 2.7 | 2.5 |

Evaluation of degree of bleeding:
None: 0, Light: 1, Moderate: 2, Severe: 3

<Measurement of Wound Area>

During exchange of the covering material, a transparent PET film was placed over the wound surface and the outline of the wound surface was traced. The film was read with an image scanner, and the obtained wound image was analyzed against an NIH image to determine the area of each wound surface. Measurements were taken for 10 days. Each daily area measurement was calculated in terms of the ratio with respect to the initial area. The average values for 9 mice are shown in FIG. 1.

<Histopathological Findings>

Separately from the aforementioned wound area measurement, other full-thickness wound models were prepared in the same manner as above and covering materials were applied and exchanged as described above. On the eighth day after creating full-thickness wounds, the mice of each group were killed under anesthesia and the wounded areas were resected with inclusion of healthy areas. The specimens were immersed in a tissue mount (product of Tissuetech) filled with OTC compound (product of Tissuetech), and were rapidly frozen in methanol cooled with dry ice. The frozen specimens were cut into thin 8 µm sections along the plane perpendicular to the skin surface using a cryostat, and were then stained with hematoxylin-eosin. The healing index was determined under microscopic examination as an indicator of reepithelialization. The thickness of the granulation tissue was also measured as an indicator of dermal regeneration. The average values for 9 mice are shown in Table 2. The healing index is the ratio of the width of the region of re-epithelialization in the wound area with respect to the width of the wound area formed by the initial resection observed in the aforementioned strips, where total healing is indicated by 1.0.

In order to detect the myofibroblasts in the granulation tissue, which are believed to be a cause of wound contracture, FITC-labeled anti-α-smooth muscle-actin monoclonal antibodies (product of Sigma) were used as the primary antibodies and biotin-labeled anti-FITC antibodies (product of Sigma) were used as the secondary antibodies, and immunostaining was carried out by the ABC method to determine the number of positive cells in a given area. The average values for 9 mice are shown in Table 2.

TABLE 2

Histopathological findings

| | Covering Material | Healing index | Granular thickness (mm) | α-SM-actin positive cells (microscope 1 visual field) |
|---|---|---|---|---|
| Example 2 | polymer-coated gauze | 0.35 | 1.2 | 2 |
| Example 3 | polymer-coated polyurethane foam material | 0.33 | 1.0 | 4 |
| Example 5 | hydrocolloid | 0.36 | 1.7 | 3 |
| Example 6 | hydrogel | 0.38 | 1.9 | 1 |
| Comparative Example 2 | gauze | 0.18 | 0.5 | 12 |
| Comparative Example 3 | polyurethane foam material | 0.22 | 0.7 | 8 |

Example 7
(Crust Adhesion Model Experiment)

Figure 2:
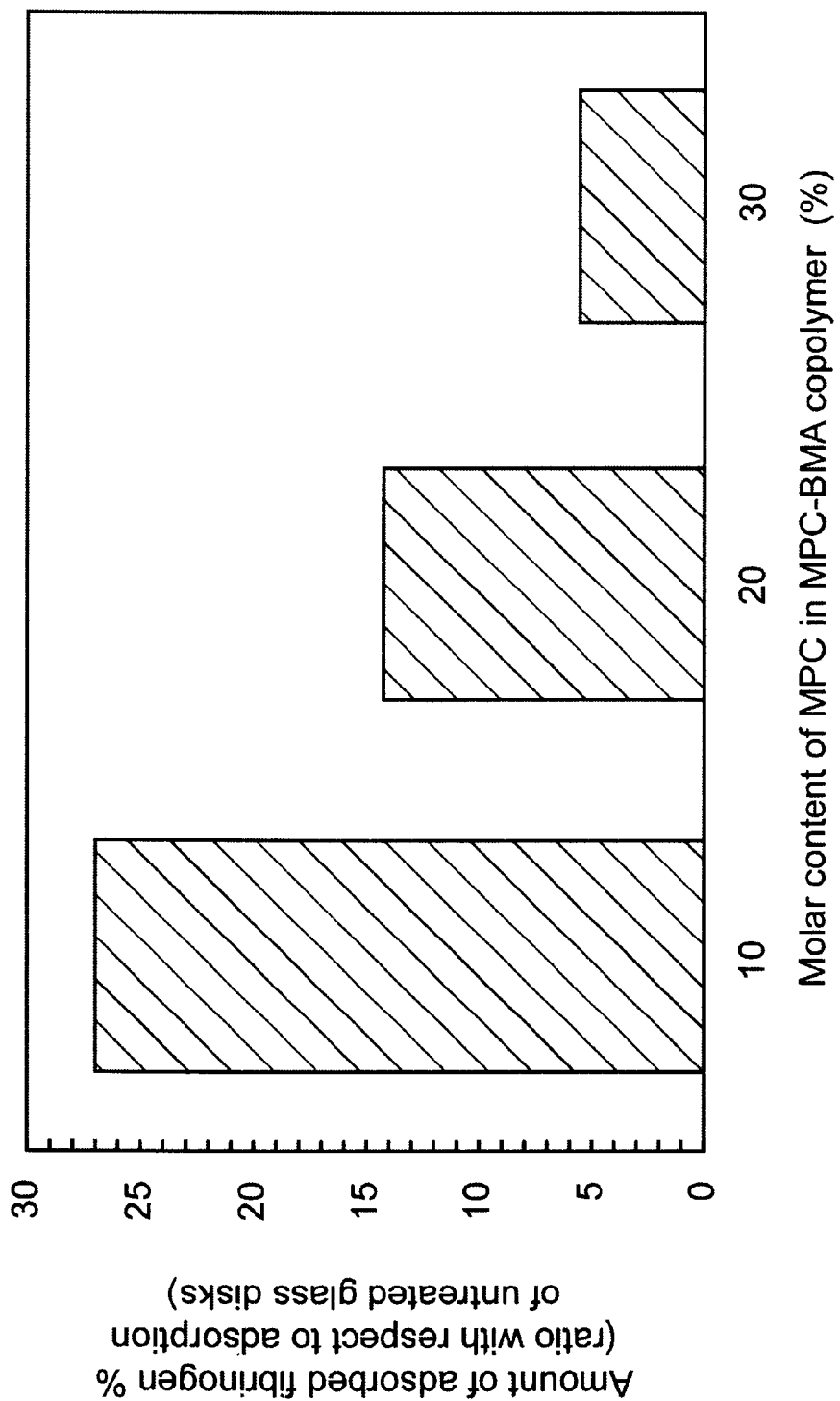
FIG. 2 is a graph showing the results of fibrinogen adsorption measurement for Example 7.

There were respectively prepared aqueous solutions containing 0.5 wt % of a homopolymer of BMA with a molecular weight of approximately 200,000, a copolymer of MPC and BMA with a molecular weight of approximately 300,000 containing 20 mol % MPC, and a copolymer of MPC and BMA with a molecular weight of approximately 480,000 containing 30 mol % MPC. Glass disks with a 7 mm diameter were immersed for 5 minutes into each solution and then washed with purified water and dried to prepare polymer-coated disks. The disks were placed in a 24-well microplate, 1 ml of rabbit plasma was added, and incubation was carried out at 37° C. for 10 minutes. The disks were rinsed 4 times with isotonic physiological saline and then incubated for 30 minutes in anti-rabbit fibrinogen antibody solution. After washing the disks, an antibody solution capable of recognizing the primary antibody labeled with horseradish peroxidase was added and incubation was carried out for 30 minutes at room temperature. After rinsing, a solution (300 µl, 0.4 mg/ml) of o-phenylenediamine (OPD) in phosphate-citrate buffer solution (300 µl, 0.6 mg/ml) was added and reaction was carried out for 10 minutes. A 200 µl aliquot of the mixture was then sampled from each well and the absorption at 450 nm was measured to quantify the adsorbed fibrinogen. The results obtained are shown in FIG. 2 in comparison with an untreated group.

Example 8 and Comparative Example 4
(Subcutaneous Implantation Test (1))

Figure 3:
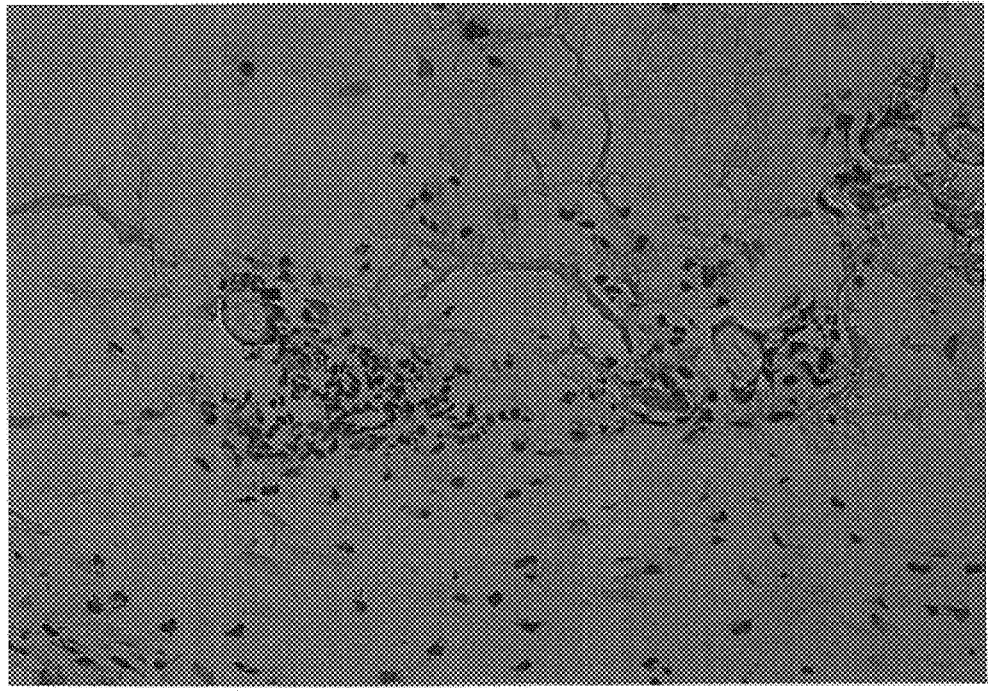
FIG. 3 is a tissue stain photograph for Comparative Example 4.

A 1 cm×1 cm×0.5 cm Japan Pharmacopoeia degreased cotton piece was immersed for 5 minutes in an aqueous solution in which a copolymer of MPC and BMA (containing 30 mol % MPC; weight average molecular weight: approximately 480,000) had been dissolved to a concentration of 1 wt %, and this was dried to obtain a coated pellet. After implanting this coated pellet (Example 8) or an uncoated 1 cm×1 cm Japan Pharmacopoeia degreased cotton pellet (Comparative Example 4) directly under the dorsal skin of ddy mice, the skin was sutured and raising was resumed. After two weeks, the pellets were removed and immersed in a tissue mount (product of Tissuetech) filled with OTC compound (product of Tissuetech), and were rapidly frozen in methanol cooled with dry ice. The frozen specimens were cut into thin 8 μm sections using a cryostat, and were then stained with hematoxylin-eosin. The observed results are shown in FIG. 3 (Comparative Example 4) and FIG. 4 (Example 8).

Figure 4:
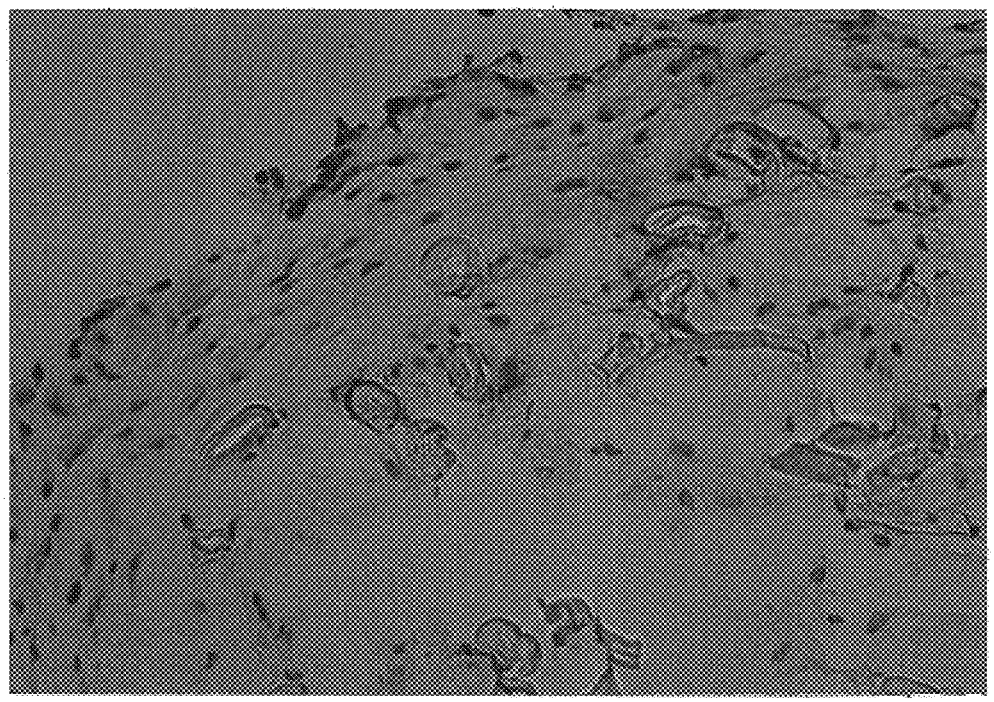
FIG. 4 is a tissue stain photograph for Example 8.

As shown in FIG. 4, virtually no adhesion of cells to the cotton fiber surface was seen even after 3 weeks, little granulation tissue, was present in the pellet and infiltration of inflammatory cells was mild, in the case of the coated pellet of Example 8 imbedded under the skin of ddy mice as compared to the untreated pellet of Comparative Example 4.

Example 9 and Comparative Example 5
(Subcutaneous Implantation Test (2))

A polyurethane disk with a diameter of 1 cm and a thickness of 1 mm was immersed for 5 minutes in an aqueous solution of a copolymer of MPC and BMA (containing 30 mol % MPC; weight average molecular weight: 480,000) at a concentration of 1 wt %, and dried to obtain a coated disk. After implanting this coated disk (Example 9) or an uncoated polyurethane disk with a diameter of 1 cm and a thickness of 1 mm (Comparative Example 5) directly under the dorsal skin of ddy mice, the skin was sutured and raising was resumed. After two weeks or three weeks, the disk was removed out and washed with physiological saline and immersed for 2 hours in a 2% glutaraldehyde solution for staining. It was again stained by further immersion for 24 hours in a 1% osmic acid solution. The disk was observed with a scanning electron microscope (Model TSM-T330A, product of JEOL Co., Ltd.). The results of observation after 3 weeks are shown in FIG. 5 (Comparative Example 5) and FIG. 6 (Example 9).

Figure 5:
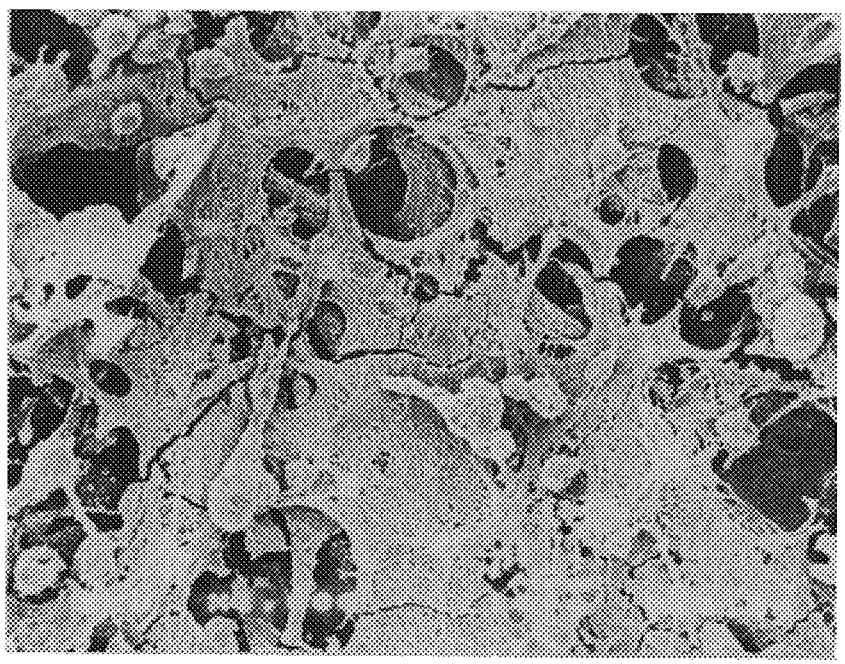
FIG. 5 is an electron microscope image for Comparative Example 5.
Figure 6:
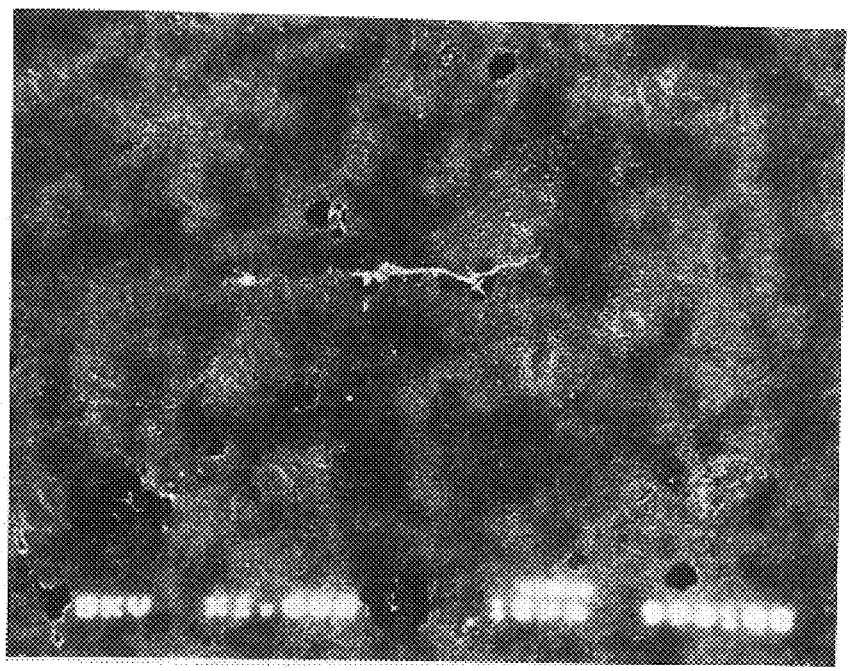
FIG. 6 is an electron microscope image for Example 9.

As shown in FIG. 5, the surface of the disk in Comparative Example 5 exhibited adhesion of multinucleated giant cells without that are implicated in activation of inflammatory cells, showing severe foreign body reaction, but the surface of the polymer-coated polyurethane disk of Example 9 showed no cells such as multinucleated giant cells in the observation results either after two weeks or after three weeks.

Example 10 and Comparative Example 6
(Peritoneal Macrophage Adhesion Test)

Culturing PET disks with a diameter of 13.5 mm (trade name: Celldisk LF1, product of Sumitomo Bakelite, K.K.) were immersed for 5 minutes in an aqueous solution of an MPC-BMA copolymer (containing 50 mol % MPC; weight average molecular weight: approximately 340,000), and dried to obtain coated disks. After intraperitoneally injecting ICR mice with 2 ml of thioglycolate medium, raising was continued for 5 days. After killing the mice, 5 ml of cold isotonic physiological saline was intraperitoneally injected and an infiltrated macrophage suspension was collected. After washing this twice with physiological saline, it was diluted approximately two-fold with RPMI 1640 medium containing 10% fetal bovine serum, it was added at 500 μl each to a 24-well culturing plate containing the coated disks (Example 10) or uncoated PET disks (Comparative Example 6). Culturing was carried out for one day at 37° C. in a 5% carbon dioxide gas incubator, and the cells on the surface of the disks obtained after washing once with isotonic physiological saline were observed with a phase contrast microscope. The observation results are shown in FIG. 7 (Comparative Example 6) and FIG. 8 (Example 10).

Figure 7:
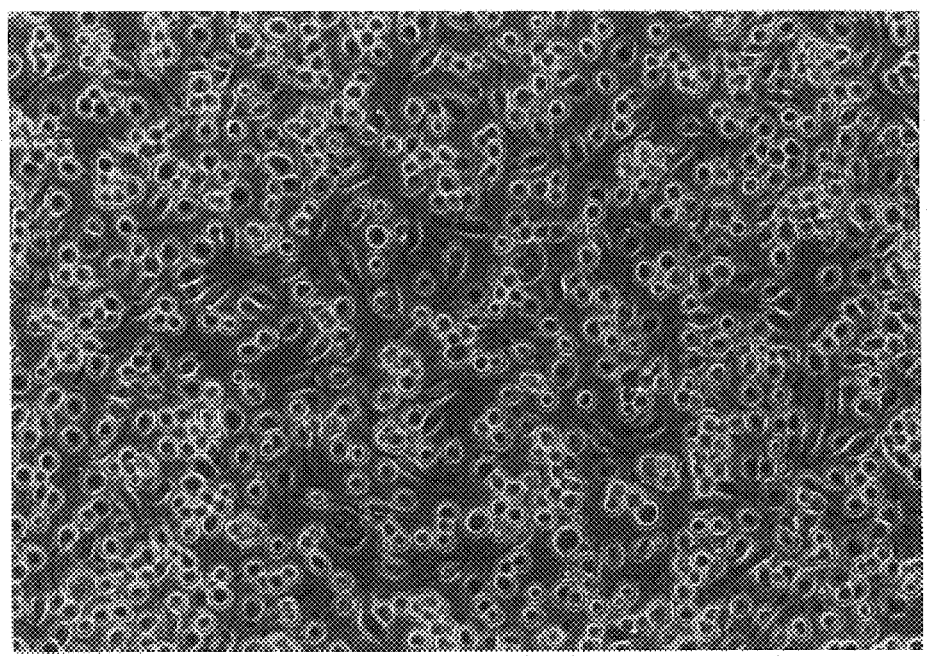
FIG. 7 is a phase contrast microscope image for Comparative Example 6.
Figure 8:
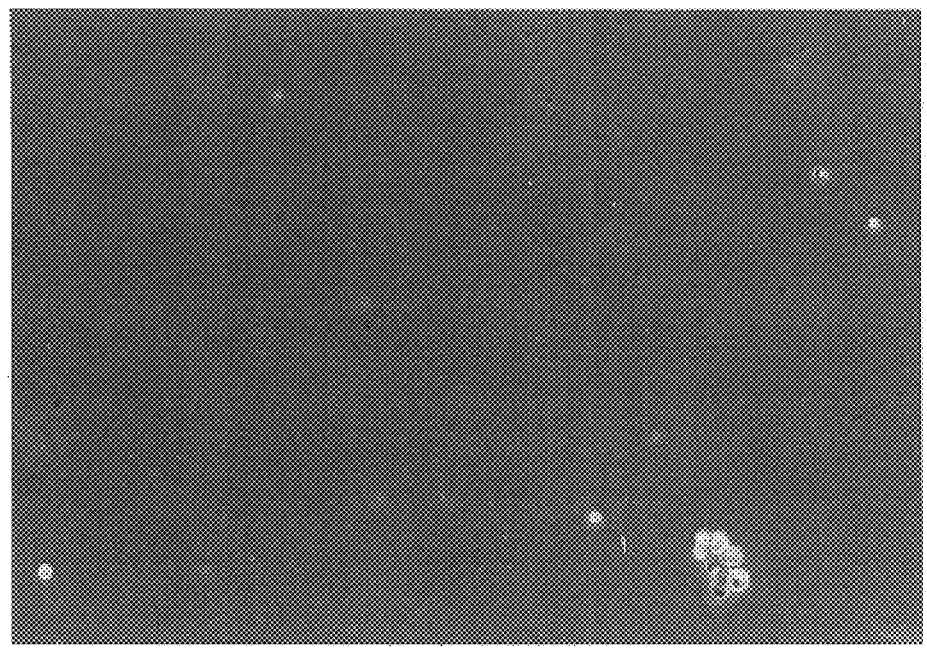
FIG. 8 is a phase contrast microscope image for Example 10.

As shown in FIG. 7, the surface of the uncoated disks was covered with macrophages, generally considered to be precursor cells of multinucleated giant cells, without interstices. In the case of the polymer-coated PET disks however, as shown in FIG. 8, absolutely no adhesion of macrophages was found.

What is claimed is:

1. A wound covering material comprising a polymer having a unit represented by the following formula (IV):

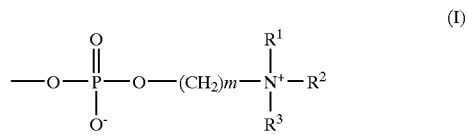

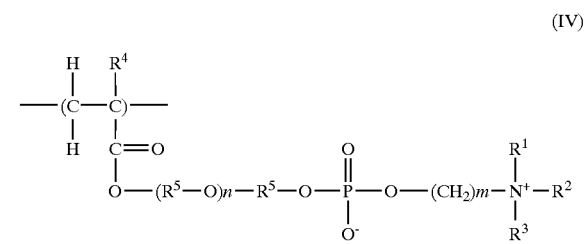

where $R^1$, $R^2$ and $R^3$ are the same or different and each represents a hydrogen atom or an alkyl group having 1 to 4 carbon atoms, m represents an integer of 2–4, $R^4$ represents a hydrogen atom, methyl group or —$CH_2$—COOH, $R^5$ represents an alkylene group having 2 to 10 carbon atoms and n represents an integer of 0–10, wherein said material is in a form of a gel.

2. A wound covering material according to claim 1, wherein said polymer is a polymer selected from the group consisting of a homopolymer of monomer (a) for the unit represented by formula (IV) above, copolymers of monomer (a) for the unit represented by formula (IV) above and monomer (b), a crosslinked polymer thereof and mixtures thereof.

3. A wound covering material according to claim 2, wherein said monomer (a) is a monomer represented by the following formula (II):

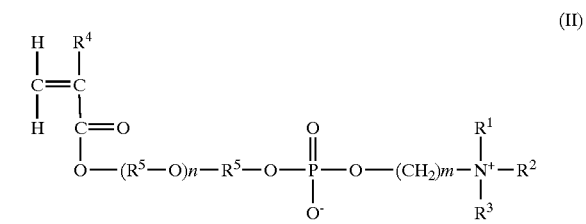

where $R^1$, $R^2$, $R^3$, $R^4$, $R^5$, n and m are the same as in formula (IV).

4. A wound covering material according to claim 2, wherein said monomer (a) is 2-methacryloyloxyethyl phosphorylcholine represented by the following formula (III):

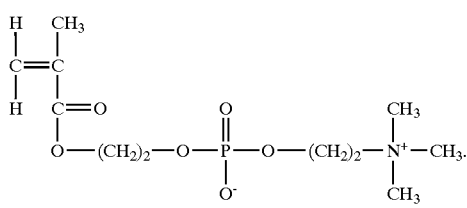

(III)

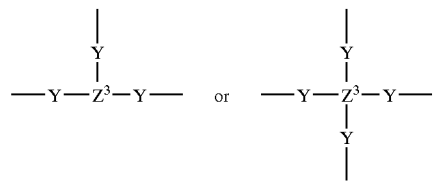

where Y represents —COO—, —CONH—, -oC6H4—, mC$_6$H$_4$—, -pC$_6$H$_4$—, —OCO— or dimethoxysilyl; $Z^1$ represents a hydrogen atom, a sodium atom, a cyano group, a vinyl group, a glycidyl group, an alkyl group having 1 to 4 carbon atoms, a hydroxyalkyl group having 2 to 4 carbon atoms, a dihydroxyalkyl group having 2 to 4 carbon atoms, a pyrrolidonyl group, a sulfonic acid group, a sodium sulfonate group, 2-ethylhexyl group, trimethoxysilylpropyl group, triethoxysilylpropyl group, methyldimethoxysilylpropyl group, an oxyalkyl group having 2 to 6 carbon atoms or a 2–20mer group that is made of oxyalkylene groups each having 2 to 6 carbon atoms and that has a hydrogen atom or methyl group at terminal thereof; $Z^2$ represents —(AO)$_r$—A— where A is an alkylene group having 1 to 12 carbon atoms and r is an integer of 0–20; and $Z^3$ represents a trivalent or tetravalent hydrocarbon group having 3 to 12 carbon atoms, and wherein the proportion of units represented by formula (V) of the total of the number of units represented by formula (IV) and the number of units represented by formula (V) in said polymer is in a range of larger than 0% and no greater than 99%, and the number average molecular weight thereof is 5,000–1,000,000.

10. A wound covering material according to claim 9, wherein X represents —Y—$Z^1$, Y represents —COO— and $Z^1$ represents an alkyl group having 1 to 4 carbon atoms.

11. A wound covering material according to claim 1, which is in a form selected from the group consisting of hydrocolloid compositions, particles, pastes, films, sheets and foam materials.

12. A wound covering material according to claim 1, which comprises a base material and said wound covering agent adhered to said base material.

13. A wound covering material according to claim 12, wherein said base material is selected from the group consisting of gauzes, nonwoven fabrics, films, sheets and foam materials.

14. A wound treatment method comprising a step of covering a wound site of a subject with a wound covering material according to claim 1 to protect the wound site.

15. A wound treatment method according to claim 14, wherein said step of covering the wound site of a subject with the wound covering material to protect the wound site includes a step of placing said wound covering material between a medical instrument and the wound site.

5. A wound covering material according to claim 2, wherein said polymer is a polymer selected from the group consisting of a copolymer of said monomer (a) and monomer (b), a crosslinked polymer thereof and mixtures thereof, and said monomer (b) is selected from the group consisting of a monofunctional monomer, a crosslinkable monomer and mixtures thereof.

6. A wound covering material according to claim 5, wherein said monomer (b) is a monofunctional monomer selected from the group consisting of hydrophilic monomers selected from the group consisting of (meth)acrylic acid, sodium(meth)acrylate, 2-hydroxyethyl(meth)acrylate, glycerol(meth)acrylate, N-vinylpyrrolidone, acrylonitrile, (meth)acrylamide, polyethyleneglycol mono(meth)acrylate, vinylbenzenesulfonic acid, sodium vinylbenzenesulfonate, itaconic acid, sodium itaconate, maleic acid, sodium maleate, fumaric acid and sodium fumarate, and methyl (meth)acrylate, ethyl(meth)acrylate, butyl(meth)acrylate, lauryl(meth)acrylate, dodecyl(meth)acrylate, stearyl(meth)acrylate, 2-ethylhexyl(meth)acrylate, styrene, vinyl acetate, and mixtures thereof.

7. A wound covering material according to claim 5, wherein said monomer (b) includes a crosslinkable monomer selected from the group consisting of a monomer with two or more polymerizable functional groups, a monomer with one or more crosslinking reactive functional groups and one or more polymerizable functional groups, and mixtures thereof.

8. A wound covering material according to claim 5, wherein said monomer (b) includes a hydrophobic monomer, and the proportion of units derived from said hydrophobic monomer in said polymer is at least 20 wt %.

9. A wound covering material according to claim 1, wherein said polymer also comprises a unit represented by the following formula (V):

(V)

where $R^6$ represents a hydrogen atom, methyl group or —CH$_2$—COOH, $R^7$ represents a hydrogen atom, a carboxyl group or an alkoxycarbonyl group having 2 to 6 carbon atoms, and X represents a group represented by —Y—$Z^1$, a crosslink represented by —Y—$Z^2$—Y— or a crosslink represented by

* * * * *